United States Patent
Scheppers et al.

[11] Patent Number: 5,869,741
[45] Date of Patent: Feb. 9, 1999

[54] MULTISAMPLE DYNAMIC HEADSPACE SAMPLER

[75] Inventors: Karl H. Scheppers, Scotts Valley; Gregory I. Rudd, Aptos, both of Calif.

[73] Assignee: Seagate Technology, Inc., Scotts Valley, Calif.

[21] Appl. No.: 892,012

[22] Filed: Jul. 14, 1997

Related U.S. Application Data

[62] Division of Ser. No. 780,886, Jan. 9, 1997, Pat. No. 5,753,791, which is a division of Ser. No. 527,292, Sep. 12, 1995, Pat. No. 5,646,334.

[51] Int. Cl.$^6$ .................................................. G01N 7/14
[52] U.S. Cl. .............................................................. 73/1.06
[58] Field of Search .......................... 73/1 G, 1 R, 23.21, 73/23.41, 23.42, 31.07, 863.12, 863.21, 864.81, 863.31, 864.73, 864.74, 1.06, 19.01, 19.02, 19.12; 422/68.1, 69, 88

[56] References Cited

U.S. PATENT DOCUMENTS

| | | |
|---|---|---|
| 4,046,014 | 9/1977 | Boehringer et al. . |
| 4,214,473 | 7/1980 | Edwards, Jr et al. ................. 73/31.03 |
| 4,388,272 | 6/1983 | Gesteland ................................. 73/19.1 |
| 4,970,891 | 11/1990 | Blevins et al. ......................... 73/19.01 |
| 5,326,708 | 7/1994 | Lewis . |

*Primary Examiner*—Robert Raevis

[57] ABSTRACT

Method and apparatus for collecting a large number of outgas samples at the same time. Specimens to be tested for outgassing are placed in throw-away widemouth bottles, and the bottles are placed in cups provide in a heating block. A custom made cap is fastened to each bottle using an O-ring. Each cap is provided with an outgassing sample collecting tube. A source of pure gas such as nitrogen or helium is connected by way of a pressure regulator and a hydrocarbon filter to a manifold. Each of the caps on each bottle is coupled to the manifold by way of a metering valve. An adsorbent is placed in each collecting tube. The gas pressure is set to between 10 and 15 psi. The flow through each collecting tube is set to a predetermined level by adjusting its metering valve and measuring the flow at the exit of the collecting tube using a flowmeter. The heating block is heated by means of a thermal tape used in conjunction with a power supply and a thermocouple inserted into a hole in the heating block. The samples are heated and held at an elevated temperature for a predetermined length of time. After the outgassing test is completed, the collecting tubes are desorbed and analyzed with the appropriate instrumentation.

2 Claims, 6 Drawing Sheets

MULTISAMPLE DYNAMIC HEADSPACE SAMPLER

This application is a division of application Ser. No. 08/780,886 filed Jan. 9, 1997, which is now U.S. Pat. No. 5,753,791, which is a division of application Ser. No. 08/527,292 filed Sep. 12, 1995, which is now U.S. Pat. No. 5,646,334.

FIELD OF THE INVENTION

The present invention relates to collecting out-gassed organic compounds given off by a sample under test and, more particularly, to an improved method and apparatus useful for collecting a plurality of outgas samples, including an improved manifold, an improved sample heater, and an improved leak-proof seal on sample containing bottles.

BACKGROUND OF THE INVENTION

It has been observed that organic compounds in the air can have a deleterious effect on electronic components. For example, even in a clean room that is substantially free of particulate matter, a semiconductor chip can be adversely affected by organic compounds in the air that settle thereon. Furthermore, it has been observed that precision mechanisms such as hard disk drives used in computers are adversely affected by organic compounds that are out-gassed from materials used in the construction thereof. A specific example is silicone or any siloxane product.

It has been found that siloxanes occur in many products. For example, some adhesives, paints, and mold release compounds outgas siloxanes when heated. It has been found that siloxanes can cause a disk drive to crash.

Thus, it has become important for the manufacturers of disk drives, and their suppliers, to carefully inspect motors, pressure sensitive adhesives, labels and other components for the presence of outgassed organic compounds. Initially, these inspections were made individually on a small scale and on a static basis using whatever laboratory equipment was available that would serve the purpose. Then, disposable jars with plastic caps were used to collect static headspace samples. However, it was found that the plastic caps were unsatisfactory. Accordingly, special aluminum caps were custom made to replace the plastic caps. It was then decided that what was needed was a multisample dynamic headspace sampler.

The term "headspace" means the space in the jar or bottle above the sample or part under test and below the cap or lid. For example, if a motor is being tested, the headspace is the space in the jar all around the motor below the cap and its seal. A static headspace sampler collects a sample of the gas in the headspace without involving a gas flow. A dynamic headspace sampler collects a sample of the gas in the headspace by using a flow of gas in the headspace.

The closest known previously existing device is a multisample purge and trap unit used in the environmental chemistry industry for monitoring volatile hydrocarbons in soils. This previously existing device is not very versatile, and almost always is connected in-line to a gas chromatograph.

DISCLOSURE OF INVENTION

In accordance with the principles of the present invention, there is provided a multichamber dynamic headspace sampler that includes a source of a gas, such as nitrogen or helium, the gas being 99.999% pure. A regulator is coupled to the source of gas. A hydrocarbon filter is coupled to the output of the regulator. Typically, the regulator may be a dual-stage 0–30 psi type of regulator. A manifold constructed of stainless steel is coupled to the regulator. Metering valves are connected to the manifold. Short, widemouth bottles having aluminum caps sealed thereto by O-rings are connected to the metering valves. The caps are also connected to a collector tube containing an adsorbent material. A heated aluminum block is provided with cups that serve as receptacles for the bottles. The aluminum block is provided with a thermocouple and a power supply for controlling the temperature thereof. A thermal insulation blanket completely covers the bottles, manifold and aluminum block.

BRIEF DESCRIPTION OF THE DRAWING

For a fuller understanding of the present invention, reference is made to the accompanying drawing taken in conjunction with the following detailed description of the invention. In the drawing.

Figure 2:
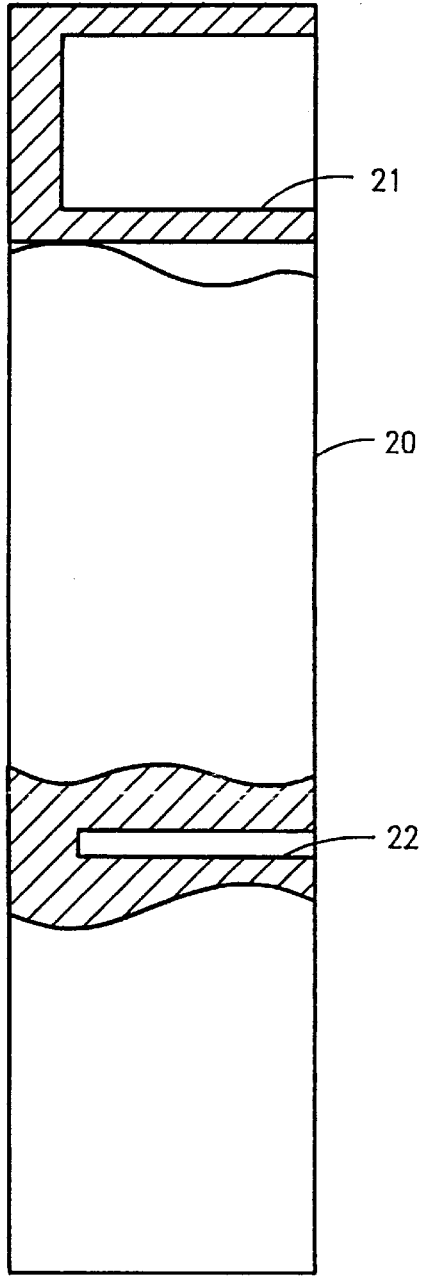
FIG. 2 is a side elevation view, partially broken away, of the heating block shown in FIG. 1.

Reference numbers refer to the same or equivalent parts of the present invention throughout the figures of the drawing.

DETAILED DESCRIPTION

Figure 1:
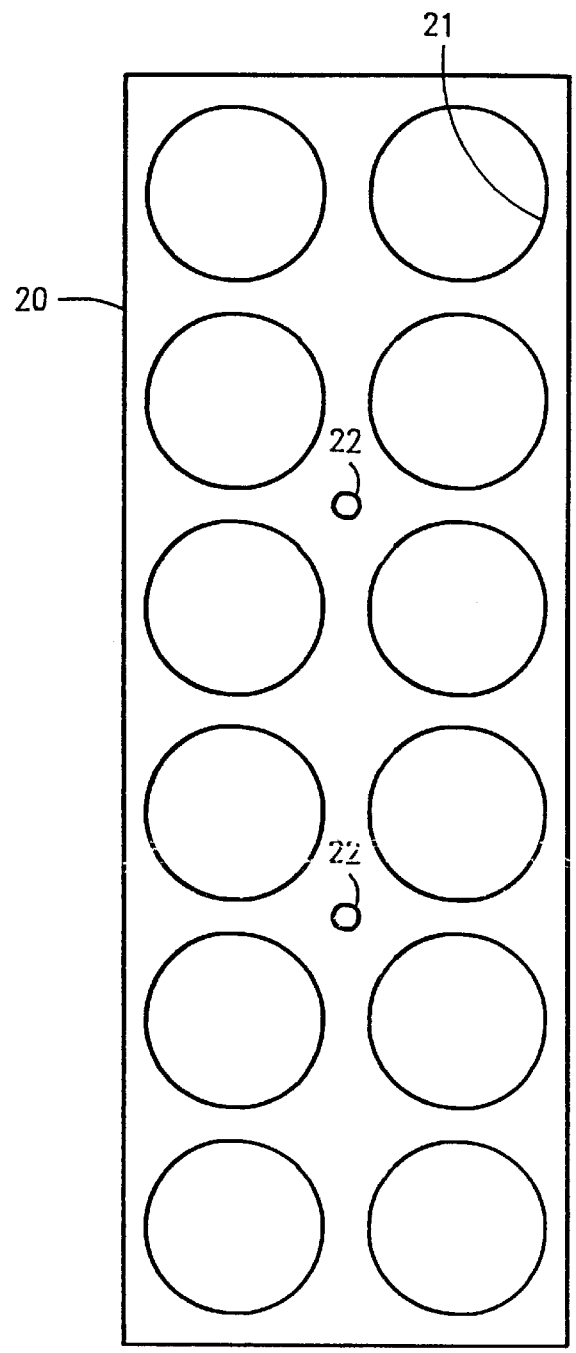
FIG. 1 is a top plan view of a heating block that is employed in an outgas test fixture in accordance with the present invention.

FIGS. 1 and 2 show a heating block 20 that is employed in a multisample dynamic headspace sampler of the present invention. FIG. 1 is a top plan view of the heating block 20, while FIG. 2 is a side elevation view. FIG. 2 is partially broken away to show certain features of the heating block 20. The heating block 20 may be made of 6061-T0 aluminum and the aluminum may be finished with a clear hard anodize. Typically the heating block 20 may be 16 inches long, 3½ inches high and 5½ inches wide. The heating block 20 is provided with 12 equally dimensioned cups 21 machined into the top surface thereof. The cups 21 may be 3.03 inches deep and 2.45 inches in diameter. Two blind holes 22 are provided in the heating block 20 that are 0.252 inches in diameter and 2.9 inches in depth.

Figure 3:
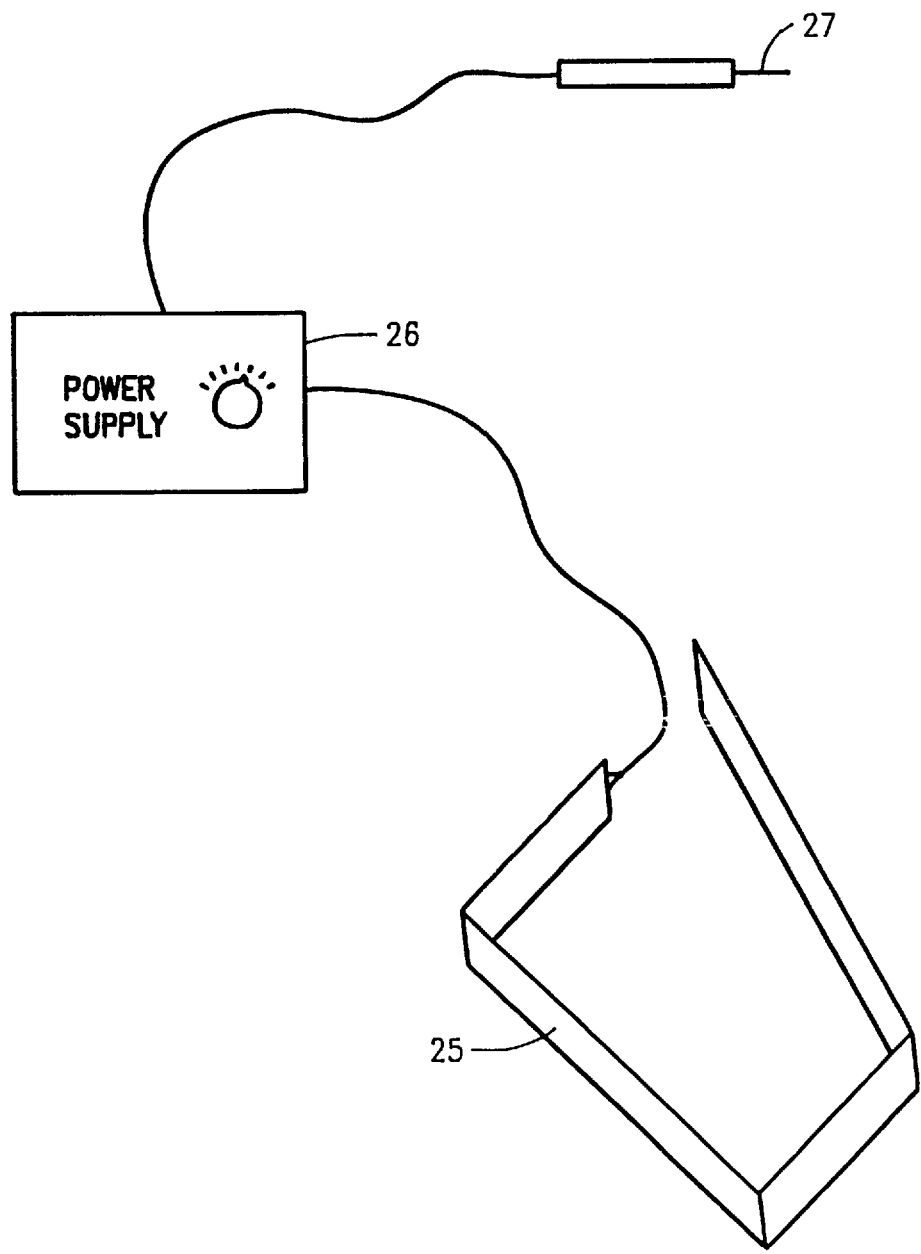
FIG. 3 is a pictorial view of a heating system that is employed with the heating block of FIGS. 1 and 2.

FIG. 3 shows a heating arrangement for use with the heating block 20 of FIGS. 1 and 2. There is provided a heating tape 25 that is at least 43 inches long. The heating tape 25 may be of a type referred to as Fibox heating tape sold by Barnstead & Thermolyn. Barnstead & Thermolyn is located at 2555 Kerper Boulevard, Dubuque, Iowa 52001.

The heating tape 25 is electrically connected to a power supply 26. The power supply 26 may be of the type called Mantle Minder II which is available from VWR Supply Company. Also attached to the power supply 26 is a thermocouple 27 which is accurate to ±2° Celsius over the range 50° to 200° C.

In operation, the heating tape 25 is wrapped around the heating block 20 and in intimate thermal contact therewith. The heating tape 25 is fastened securely to the outside of the heating block 20. The thermocouple 27 is placed in one of the blind holes 22 of the heating block 20. The power supply 26 is set for the desired temperature and the thermocouple 27 and the heating tape 25 maintain the heating block 20 to the desired temperature.

Figure 4:
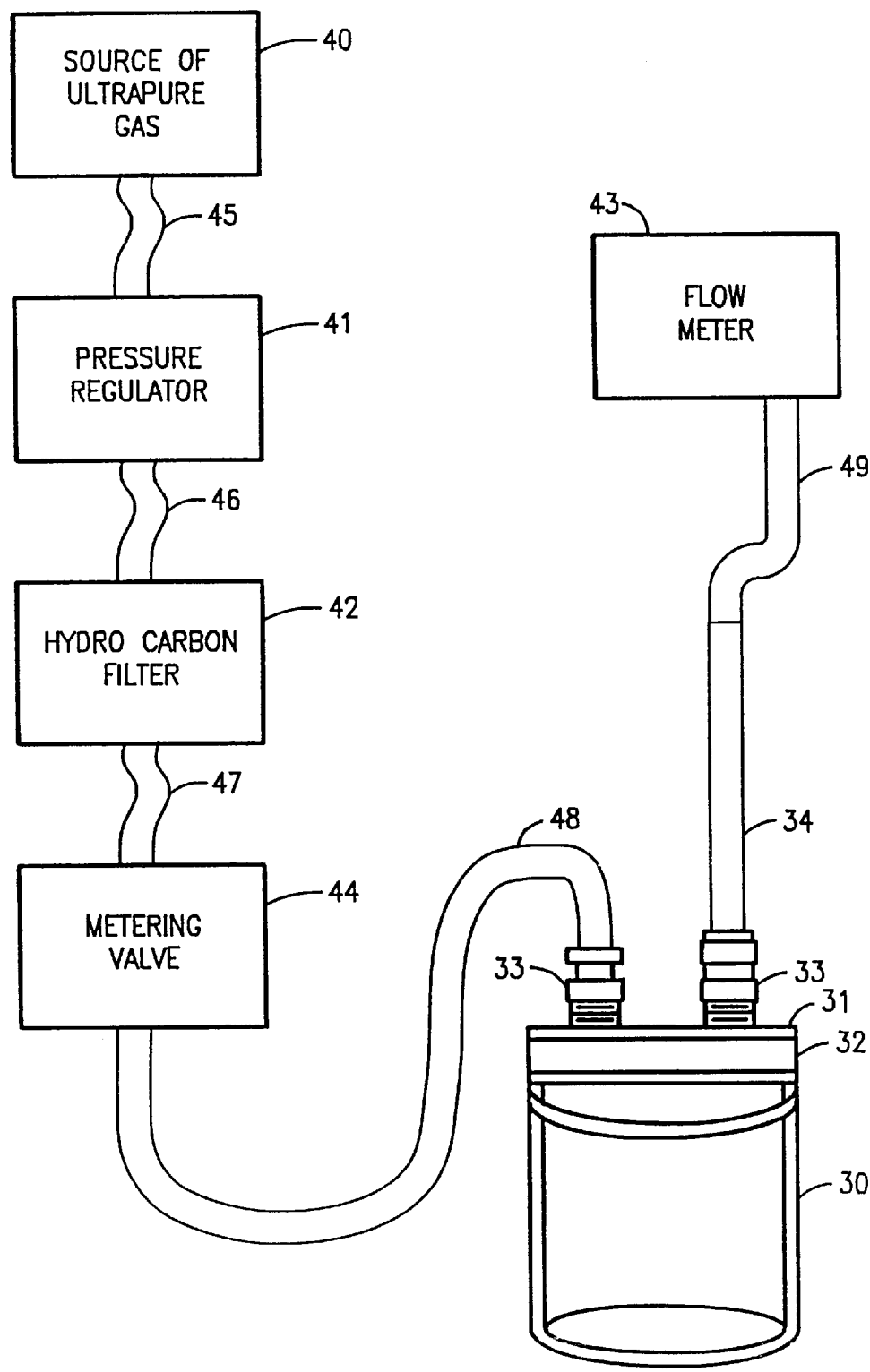
FIG. 4 is a schematic diagram illustrating dynamic gas flow through a widemouth specimen bottle and collection tube employed in an outgas test fixture in accordance with the present invention.

FIG. 4 is a schematic diagram illustrating dynamic gas flow through a bottle 30 having a capacity of 125 ml., and having a wide mouth. The top of the bottle 30 is threaded and has a cap 31 fitted thereto. The cap 31 is made of 6061-T0 aluminum and is knurled around the outside edge at 32. The cap 31 is provided with threaded openings into which are screwed two fittings 33 of the type made by Swagelock and described as Ultra Torr. The fittings 33 are ¼ inch Ultra Torr ⅛ inch pipe threads. A tube 34 is connected to one of the fittings 33. The tube 34 may be made of stainless steel and may be a Part No. L4270123 manufactured by Perkin Elmer, for example, although there are many other tubes that will serve. Almost any 6 mm. O.D. tube constructed of glass or stainless steel can be used. A source 40 of ultra pure gas is provided. The gas should be 99.999% pure, and may be either helium or nitrogen gas, for example. The gas source 40 is connected to a pressure regulator 41 by a tubing 45. The pressure regulator 41 may be a dual stage regulator, 0–30 psi. The pressure regulator 41 is connected by a tubing 46 to a hydrocarbon filter 42 which may be a hydrocarbon trap Part No. 8C2-2445 which is supplied by Supelco, Inc. The filter 42 is connected by a tubing 47 to a metering valve 44 which is, in turn, connected by a tubing 48 to one of the fittings 33 on the bottle 30. In connecting the gas source 40, the pressure regulator 41, the hydrocarbon filter 42, the metering valve 44 and the fitting 33, ⅛ inch stainless steel or copper tubing 45, 46, 47, 48 and appropriate connectors of the type manufactured by Swagelock should be used. The metering valve 44 may be an S series fine metering angle valve sold by Nupro as Part No. SS-SM2-S2-A. A flow meter 43 is connected to the exit of the tube 34 by a tubing 49. The flow meter 43 may be one identified as Humonics Veri-Flow 500 or equivalent. The tubing 49 should also be ⅛ inch stainless steel or copper tubing.

In operation, a specimen whose outgassing is to be tested is placed in the bottle 30, a suitable adsorbent is put into the tube 34. The gas pressure of the source 40 is set between 10 and 15 psi. After the gas pressure has been set to between 10 and 15 psi, the flow is set to the desired level using the metering valve 44 while measuring the flow at the exit of the adsorbent tube 34 by means of the flow meter 43. Flow rates are typically set between 50 and 250 ml. per minute. The specimen in the bottle 30 is heated to cause outgassing and is held at an elevated temperature for between 3 and 24 hours to collect a sample of the a outgassed organic material in the tube 34.

Figure 5:
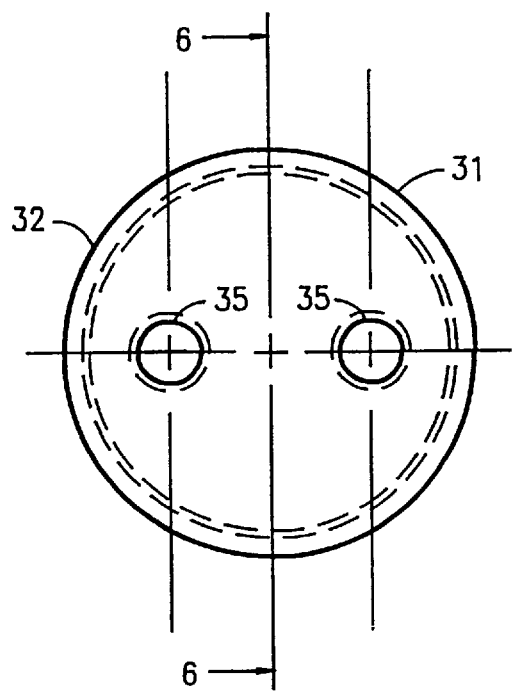
FIG. 5 is a top plan view of a custom made cap for the widemouth specimen bottle shown in FIG. 4.
Figure 6:
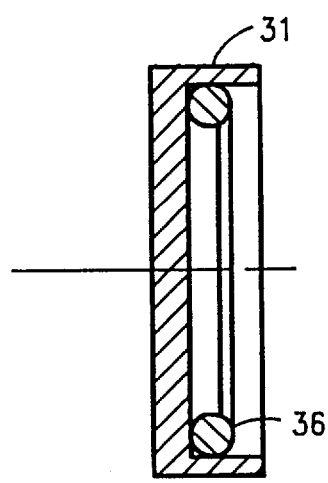
FIG. 6 is a side elevation view in cross-section taken along the line 6—6 of FIG. 5.

FIGS. 5 and 6 illustrate details of the cap 31 shown in FIG. 4. FIG. 5 is a top plan view of the cap 31, while FIG. 6 is a section view of FIG. 5. The cap 31 has a knurled exterior at 32, and is provided with two threaded openings 35 that have a ⅛-27 NPT pipe thread. The interior of the cap 31 is threaded with a 56×4.6 mm jar thread. As may be seen in FIG. 6, the cap 31 is provided with an O-ring 36. This O-ring 36 typically has a thickness of 0.10 inches and an outer diameter of 2.28 inches, and is made of a fluoroelastomer copolymer of hexafluoropropylene and vinylidene fluoride. this material is used because it does not contaminate the outgas sample. These materials are typically sold under the trade name Viton. A satisfactory O-ring 36 is sold as Part No. 2-226,V75 by Ace Seal Co. It will be understood that it is necessary to use pure materials in the construction of the outgas test fixture of the present invention so as not to contribute unwanted materials to the outgassed test sample.

Figure 7:
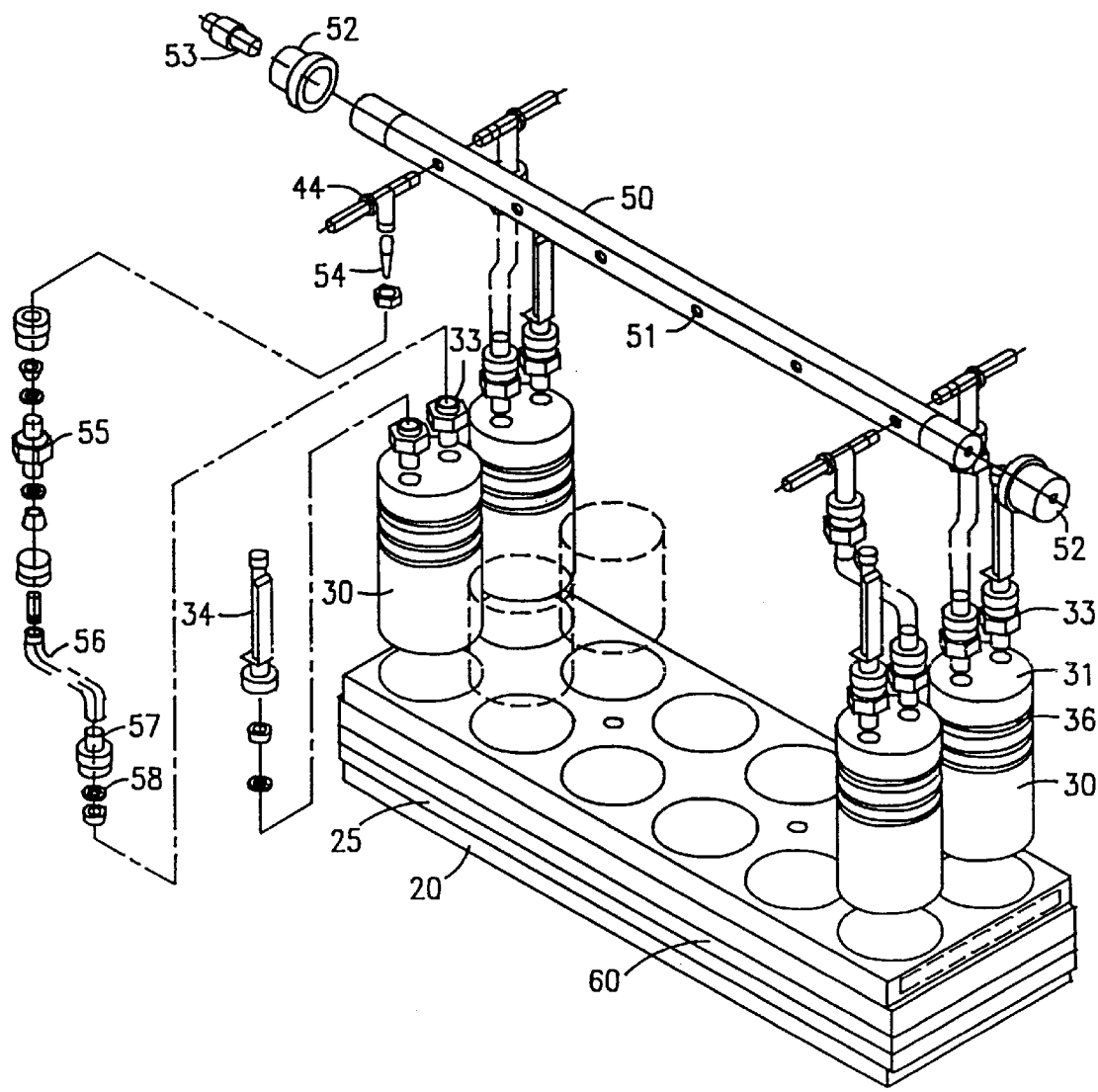
FIG. 7 is an exploded perspective view of an outgas test fixture constructed in accordance with the principles of the present invention.

FIG. 7 is an exploded perspective view of an outgas test fixture for testing more than one specimen at a time. This is accomplished by the use of a manifold 50 to distribute gas to a plurality of bottles 30. The manifold 50 comprises a stainless steel pipe ½ inch in diameter and 17 inches long. The manifold is provided with 12 threaded holes 51, six holes 51 along each side of the manifold 50. The holes 51 are threaded with a ⅛-27 NPT thread. A pipe cap 52 is provided at each end of the manifold 50. One of the pipe caps 52 is provided with a connector 53. This connector 53 may be Part No. SS-200-1-2 manufactured by Swagelock and identified as a ⅛ inch tube-⅛ NPT connector. The connector 53 is connected to the hydrocarbon filter 42 shown in FIG. 4. Each hole 51 is provided with a metering valve 44 as shown in FIG. 4. The metering valve 44 is coupled to a port connector 54. The port connector 54 may be Part No. SS-201-PC manufactured by Swagelock and described as a ⅛—⅛ port connector. The port connector 54 is connected to a union 55. The union 55 may be a Part No. SS-4-UT-6-200 manufactured by Swagelock and described as a ⅛-¼ tubing union. The union 55 is connected to a flexible tubing 56. The flexible tubing 56 may be a Part No. 321-4-X-4 manufactured by Cajon and described as stainless steel flexible tubing. The other end of the flexible tubing 56 connects to an O-ring adapter 57. The O-ring adapter 57 may be Part No. 304-4-XOA manufactured by Cajon and described as an O-ring adapter. The O-ring adapter 57 attaches to the fitting 33 on the bottle 30. An O-ring 58 is compressed when the O-ring adapter is connected to the fitting 33. The O-ring 58 is of a size to fit the O-ring adapter 57 and is also made of the elastomer described hereinabove and sold under the trade name Viton. A satisfactory O-ring 58 is sold as Part No. 2-010,V75 by Ace Seal Co.

Referring to FIG. 3 taken in conjunction with FIG. 7, the heating block 20 is provided with cups 21 to receive the bottles 30. The heating tape 25 is wrapped around the heating block 20. A compression band 60 is disposed completely around the heating block 20 and clamps the heating tape 25 into intimate heat conductive contact with the heating block 20. The compression band 60 may be a large radiator hose clamp as is used in the automotive industry, if desired.

The outgas test fixture shown in FIG. 7 may be used to quantitatively analyze the amount of off-gassed organic compounds over a broad temperature range of from 25° C. to 200° C. The choice of the appropriate adsorbent, temperatures, flow rate and method of analysis is up to the analyst and should be selected with the objective of obtaining the highest recovery and reproducibility for the target analytes under the chosen absorption and desorption conditions. The word "analyte" is used herein to mean the specific materials or off-gassed organic compounds that are to be analyzed.

As mentioned hereinbefore, almost any 6 mm. O.D. tube constructed of glass or stainless steel can be used as a holder for the sorbent. Silanized glass wool should be used to pack the sorbent. Either thermal desorption or solvent desorption can be used to prepare the sample for instrumental analysis.

The following is a description of the steps to be followed in using the outgas test fixture shown in FIG. 7. Preclean the stainless steel fittings 33 and aluminum caps 31 prior to assembly by sonic cleaning in an acetone bath, followed by heating. Assemble the outgas test fixture as shown in FIG. 7 using PTFE Teflon tape on all pipe threads. Connect the outgas test fixture at connector 53 to a hydrocarbon filter 42 as shown in FIG. 4. Then connect the hydrocarbon filter 42 to a source 40 of ultra pure gas that is controlled with a regulator 41, as shown in FIG. 4. Use stainless steel or copper tubing and appropriate Swagelock connectors. Preheat the heating block 20 to about 15° below the final target temperature. This is usually done by setting the thermostat on the power supply 26 to the desired temperature and waiting one hour. Without insulation the block 20 will usually equilibrate 10 to 15° below the target temperature.

Place the samples whose outgassing is to be tested in the wide mouth bottles 30. Up to 10 samples can be run if two positions are reserved for a method blank and a spike. The term "method blank" refers to an empty sample bottle 30 and its collection tube 34 that is tested along with the other samples. The method blank is tested in the identical manner as a sample, but it does not contain a sample. The method blank is also sometimes referred to as a "system" blank. The method blank indicates the baseline contamination level.

The term "spike" refers to placing a known amount of a compound or compounds in the sample bottle 30 and then analyzing the "spiked" collection tube 34, as if it were a sample. The measured amount of analyte or analytes can be compared to the known amount for a determination of the recovery factor for each analyte. The recovery factor equals $$= \frac{\text{(The amount measured)} \times 100}{\text{(The amount injected in spike)}}$$

Inject a suitable internal standard into all bottles 30. An internal standard is a known amount of a single compound that is intentionally added to all samples. The recovery factor has been determined for this compound. The overall reliability of the results from a particular sample run is assessed in part by how well the internal standard recovery results match with what is normally expected for that compound when the system is known to be functioning optimally.

Screw the bottles 30 onto the aluminum caps 31 using Viton O-rings 36. Insert one of the 6 mm. O.D. adsorbent containing tubes 34 into the Ultra Torr fitting 33 and finger tighten the nut. Mark the tube 34 and the aluminum cap 31 with the appropriate position number. Turn the gas pressure to between 10 and 15 psi. Set the flow to the desired level using the metering valves 44 while measuring the flow at the exit of the adsorbent tube using the flow meter 43. Ideally, all flow rates should be the same within ±2 ml. per minute. Typically good results can be obtained with flow rates between 50 and 250 ml. per minute. Place the bottles 30 into the heating block 20 and record the time and temperature in a log book.

Figure 8:
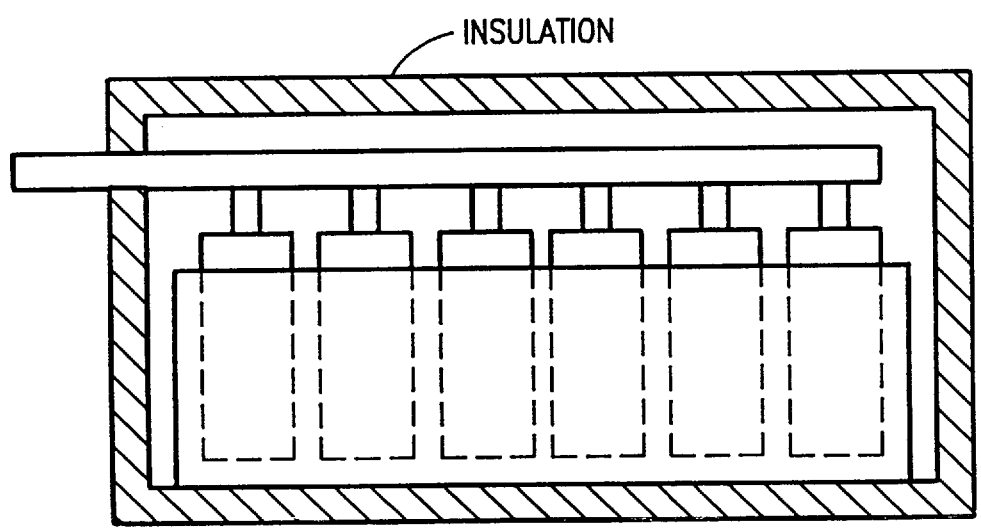
FIG. 8 is a side view partly in cross-section of the outgas test fixture of FIG. 7 blanketed by a layer of insulation.

Add a layer of insulation as shown in FIG. 8 to the top of the outgas test fixture so as to completely blanket the device. The insulation may be any conventional insulation such as the fiberglass insulation batting used in the walls of houses and other buildings, for example. Record the time and temperature at desired intervals. Typically the target temperature can be reached within 30 minutes after adding the insulation. The temperature stability is usually ±2° C. Typical run times for sample collection are between 3 and 24 hours. End the experiment by reversing the order of the steps. Desorb the tube 34 and then analyze the contents with the appropriate instrumentation.

Calibration procedures will vary depending on the application. The following is a general calibration procedure. Prepare a calibration curve for each analyte and the internal standard on the analysis instrument. Use the calibration curve to quantify the amount of material desorbed from the adsorbent. Use the data from the spike run to determine the recovery for each target analyte.

In the reporting procedure, report the quantitative values obtained from the spike run, along with the percent recovery. For each sample, report the values obtained for each analyte, along with the measured value for the internal standard.

The measured values obtained from spikes and spike duplicates can be used to assess the accuracy and precision of the measurement technique. Spike duplicates are duplicate runs of the spike referred to hereinabove. As an example, 2500 nanograms of hexadecane was used as an internal standard and collected at 80° C. for 3 hours. Each tube was then thermally desorbed and analyzed by a gas chromatograph equipped with a mass spectrometer detector. The results were as shown in Table I. Table I illustrates that for hexadecane, the recovery is 100% indicating that all of the hexadecane placed in the bottle 30 was collected into adsorbent in the tube 34 and accurately analyzed. The relative standard deviation (RSD) was below 2%, indicating a high degree of precision.

Relative standard deviation (RSD) is a mathematical way of describing the variation in a group of measurements or numbers.

$$RSD = \frac{100s}{\overline{X}}$$

$$\text{where } s = \sqrt{\frac{\Sigma_i X_i^2}{n-1} - \frac{(\Sigma X_i)^2}{n(n-1)}}$$

With a stable compound and stable analysis conditions, the method, accuracy, and precision can be kept below ±5%.

TABLE I

| Amount of Spike hexadecane (ng) | Amount Measured hexadecane (ng) | % Recovery | Avg. Recov. | % RSD |
|---|---|---|---|---|
| 2500 | 2476 | 99.04 | | |
| 2500 | 2495 | 99.8 | | |
| 2500 | 2568 | 102.72 | | |
| | | | 100.52 | 1.91 |

The objective for this improved outgas method is to improve recovery precision and to improve dilution factor precision. That is to say the outgas method of the present invention has improved sensitivity relative to previous methods used. These two factors account for 33% of the random error, while the analysis steps contribute only 10%. A test with ±20% repeatability may be made possible by the method and apparatus of the present invention.

Some features of the outgas test fixture of the present invention are that the sample chamber bottle 30 does not require cleaning. It is disposable. The sample bottle 30 is sealed with Viton O-rings 36 which are made of a pure form of elastomer and do not contribute contaminates or contaminants to the sample. The heating block 20 maintains temperatures to ±2° C. The tubes 34 accommodate a variety of adsorbents. Either thermal or solvent desorption can be used for analysis by Fourier transform infrared spectroscopy, atomic absorption spectroscopy, ion chromatography, or supercritical fluid chromatography.

The present invention has been particularly shown and described with respect to a preferred embodiment and features thereof. However, it should be readily apparent to those of ordinary skill in the art that various changes and modifications in form and detail may be made without departing from the spirit and scope of the invention as set forth in the appended claims. The invention illustratively disclosed herein may be practiced without any element which is not specifically disclosed herein.

What is claimed is:

1. Apparatus for analyzing off-gassed organic compounds from a plurality of specimens, said apparatus comprising:

a plurality of sampling chambers adapted to receive specimens for testing, reserving one of said sampling chambers for a spike;

an adsorbent containing tube coupled to an exit aperture of each of sampling chambers;

apparatus for applying a gas under pressure to entrance apertures of each of said sampling chambers;

apparatus for setting gas flow to a predetermined level at an inlet of each of said adsorbent containing tubes; and apparatus for heating said plurality of said sampling chambers to a predetermined temperature;

whereby following heating of said specimens, the contents of said adsorbent containing tubes may be desorbed and analyzed using instrumentation capable of identifying organic compounds.

2. Apparatus for analyzing off-gassed organic compounds from a plurality of specimens, said apparatus comprising:

a plurality of sampling chambers adapted to receive specimens for testing, reserving one of said sampling chambers for a method blank, and reserving one of said chambers for a spike;

said sampling chambers being adapted to receive an injection of an internal standard organic compound;

an adsorbent containing tube coupled to an exit aperture of each of sampling chambers;

apparatus for applying a gas under pressure to entrance apertures of each of said sampling chambers;

apparatus for setting gas flow to a predetermined level at an inlet of each of said adsorbent containing tubes; and apparatus for heating said plurality of said sampling chambers to a predetermined temperature;

whereby following heating of said specimens, the contents of said adsorbent containing tubes may be desorbed and analyzed using instrumentation capable of identifying organic compounds.

\* \* \* \* \*